(12) United States Patent
Okamoto

(10) Patent No.: US 8,915,593 B2
(45) Date of Patent: Dec. 23, 2014

(54) OPHTHALMOLOGIC APPARATUS

(75) Inventor: Keiichiro Okamoto, Nagoya (JP)

(73) Assignee: Tomey Corporation, Nagoya-Shi, Aichi-Ken (JP)

( * ) Notice: Subject to any disclaimer, the term of this patent is extended or adjusted under 35 U.S.C. 154(b) by 0 days.

(21) Appl. No.: 13/362,164

(22) Filed: Jan. 31, 2012

(65) Prior Publication Data

US 2012/0200825 A1   Aug. 9, 2012

(30) Foreign Application Priority Data

Feb. 4, 2011   (JP) .................................. 2011-023188

(51) Int. Cl.
*A61B 3/14* (2006.01)
*A61B 3/15* (2006.01)
*A61B 3/113* (2006.01)
*A61B 3/12* (2006.01)

(52) U.S. Cl.
CPC .................. *A61B 3/154* (2013.01); *A61B 3/113* (2013.01); *A61B 3/1225* (2013.01); *A61B 3/152* (2013.01); *A61B 3/14* (2013.01)
USPC ............ 351/208; 351/206; 351/210; 351/221

(58) Field of Classification Search
CPC ........ A61B 3/14; A61B 3/1225; A61B 3/152; A61B 3/113
USPC .................................................. 351/200–246
See application file for complete search history.

(56) References Cited

U.S. PATENT DOCUMENTS

| | | |
|---|---|---|
| 5,807,273 A | 9/1998 | Suzuki |
| 2008/0151188 A1* | 6/2008 | Kawai et al. .................. 351/206 |
| 2010/0110172 A1 | 5/2010 | Satake |
| 2010/0315590 A1* | 12/2010 | Ueno ............................. 351/206 |
| 2011/0075098 A1* | 3/2011 | Endo et al. ..................... 351/212 |

(Continued)

FOREIGN PATENT DOCUMENTS

| | | |
|---|---|---|
| EP | 2090222 | 8/2009 |
| JP | 9-149884 | 6/1997 |

(Continued)

OTHER PUBLICATIONS

Translation of Japanese Patent Application No. JP2011-23188 prepared by Hiroaki Murase of Kai-U Patent Law Firm, Aug. 6, 2013, 22 pages.

(Continued)

*Primary Examiner* — Scott J Sugarman
*Assistant Examiner* — Daniele Manikeu
(74) *Attorney, Agent, or Firm* — Vierra Magen Marcus LLP

(57) ABSTRACT

An ophthalmologic apparatus comprises an optical measurement system that radiates measurement light to an eye to be examined, an imaging unit that takes a cross sectional image of the eye by using reflected light of the measurement light from the eye, and a controller that controls the optical measurement system and the imaging unit. When the optical measurement system is positioned at a measurement position, the controller obtains a two-dimensional cross sectional image by the imaging device. One axis of the two-dimensional cross sectional image extends in a vertical direction of the eye, and another axis of the two-dimensional cross sectional image extends in a depth direction of the eye. The controller determines whether the eye is in an examinable state or not based on the two-dimensional cross sectional image.

4 Claims, 4 Drawing Sheets

(56) References Cited

U.S. PATENT DOCUMENTS

| | | | |
|---|---|---|---|
| 2011/0181702 A1 | 7/2011 | Hauger et al. | |
| 2011/0228222 A1 | 9/2011 | Kobayashi | |
| 2011/0267582 A1* | 11/2011 | Endo et al. | 351/206 |
| 2011/0292339 A1* | 12/2011 | Itoh | 351/206 |
| 2012/0188357 A1 | 7/2012 | Hiramatsu et al. | |

FOREIGN PATENT DOCUMENTS

| | | | |
|---|---|---|---|
| JP | 10-85188 | | 4/1998 |
| JP | 2000-157493 | | 6/2000 |
| JP | 2010-110656 | | 5/2010 |
| JP | 2010110393 A | | 5/2010 |
| JP | 2010167268 A | | 8/2010 |
| JP | 2011025046 A | | 2/2011 |
| JP | 2011120892 A | | 6/2011 |
| JP | 2011229842 A | * | 11/2011 |
| WO | 2010073655 A1 | | 7/2010 |

OTHER PUBLICATIONS

Certification of Translation, Hiroaki Murase of Kai-U Patent Law Firm, Aug. 6, 2013, 1 page.
English Translation of Abstract of Japanese Patent Application No. JP2010-110656.
Machine translation of Japanese Patent Application No. JP2010-110656 prepared by the Japanese Patent Office.
English Translation of Abstract of Japanese Patent Application No. JP9-149884.
Machine translation of Japanese Patent Application No. JP9-149884 prepared by the Japanese Patent Office.
English Translation of Abstract of Japanese Patent Application No. JP10-85188.
Machine translation of Japanese Patent Application No. JP10-85188 prepared by the Japanese Patent Office.
English Translation of Abstract of Japanese Patent Application No. JP2000-157493.
Machine translation of Japanese Patent Application No. JP2000-157493 prepared by the Japanese Patent Office.
Office Action dated Jul. 15, 2014 in Japanese Patent Application No. JP2011023188, with English Translation, 6 pages.
English abstract and patent family list of JP2010-110393 published May 20, 2010, 3 pages.
Machine translation of JP2010-110393 published May 20, 2010, 18 pages.
English abstract and patent family list of JP2010-167268 published Aug. 5, 2010, 4 pages.
Machine translation of JP2010-167268 published Aug. 5, 2010, 14 pages.
English abstract and patent family list of JP2011-120892 published Jun. 23, 2011, 2 pages.
Machine translation of JP2011-120892 published Jun. 23, 2011, 13 pages.
English abstract and patent family list of JP2011-025046 published Feb. 10, 2011, 2 pages.
Machine translation of JP2011-025046 published Feb. 10, 2011, 12 pages.

* cited by examiner

OPHTHALMOLOGIC APPARATUS

CROSS-REFERENCE TO RELATED APPLICATION

This application claims priority to Japanese Patent Application No. 2011-023188 filed on Feb. 4, 2011, the contents of which are hereby incorporated by reference into the present application.

TECHNICAL FIELD

The present teachings relate to an ophthalmologic apparatus for eye examination.

DESCRIPTION OF RELATED ART

When eye examination is performed, accurate examination is sometimes impossible due to a state of an eye to be examined. For example, where a cornea shape or angle shape of the eye is examined, when an eyelid is not completely open or eyelashes block the imaging region, images of the cornea or angle of the eye cannot be accurately picked up and accurate examination cannot be conducted. Accordingly, an ophthalmologic apparatus has been disclosed that is provided with a function of detecting an eyelid opening state of the eye to be examined when eye examination is conducted, and determining whether the eye to be examined is in the examinable state or not (e.g., Japanese Patent Application Publication Nos. H9-149884 and H10-85188).

With the technique described in Japanese Patent Application Publication Nos. H9-149884 and H10-85188, light is radiated to the eye to be examined and the eyelid opening state of the eye is determined by the light intensity of the reflected image of the light (bright spot) from the cornea surface of the eye. For this reason, when the eye is dry, opaque, or of an irregular shape, the light intensity of the reflected image from the cornea surface is low even when the eyelid is sufficiently open. As a result, whether the eye is in the examinable state or not cannot be accurately determined.

BRIEF SUMMARY OF INVENTION

It is an object of the present teachings to provide an ophthalmologic apparatus that can accurately determine whether the eye to be examined is in the examinable state or not even when the eye is dry, opaque, or of an irregular shape.

The ophthalmologic apparatus disclosed in the present description includes: an optical measurement system that radiates measurement light to an eye to be examined, a drive unit that moves the optical measurement system relative to the eye, an imaging unit that takes a cross sectional image of the eye by using reflected light of the measurement light from the eye, and a controller that controls the drive unit and the imaging unit. When the drive unit positions the optical measurement system relative to the eye, the controller obtains a two-dimensional cross sectional image by the imaging device, one axis of the two-dimensional cross sectional image extending in a vertical direction of the eye, and another axis of the two-dimensional cross sectional image extending in a depth direction of the eye, and the controller determines whether the eye is in an examinable state or not based on the two-dimensional cross sectional image.

In such an ophthalmologic apparatus, the two-dimensional cross sectional image, in the vertical direction and depth direction of the eye is acquired when the optical measurement system is positioned relative to the eye. When the eye is blocked by the eyelid or eyelashes, nothing can be seen in the portion of the two-dimensional cross sectional image picked up by the imaging device that is blocked by the eyelid or eyelashes, and therefore it is possible to determine whether the eye is blocked by the eyelid or eyelashes. As a consequence, whether the eye is in the examinable state or not can be determined on the basis of the two-dimensional cross sectional image acquired when positioning is made. Since in such ophthalmologic apparatus the determination is made by using the two-dimensional cross sectional image obtained by the imaging device, whether the eye is in the examinable state can be accurately determined even when the eye is dry, opaque, or of an irregular shape.

DETAILED DESCRIPTION OF INVENTION

Figure 1:
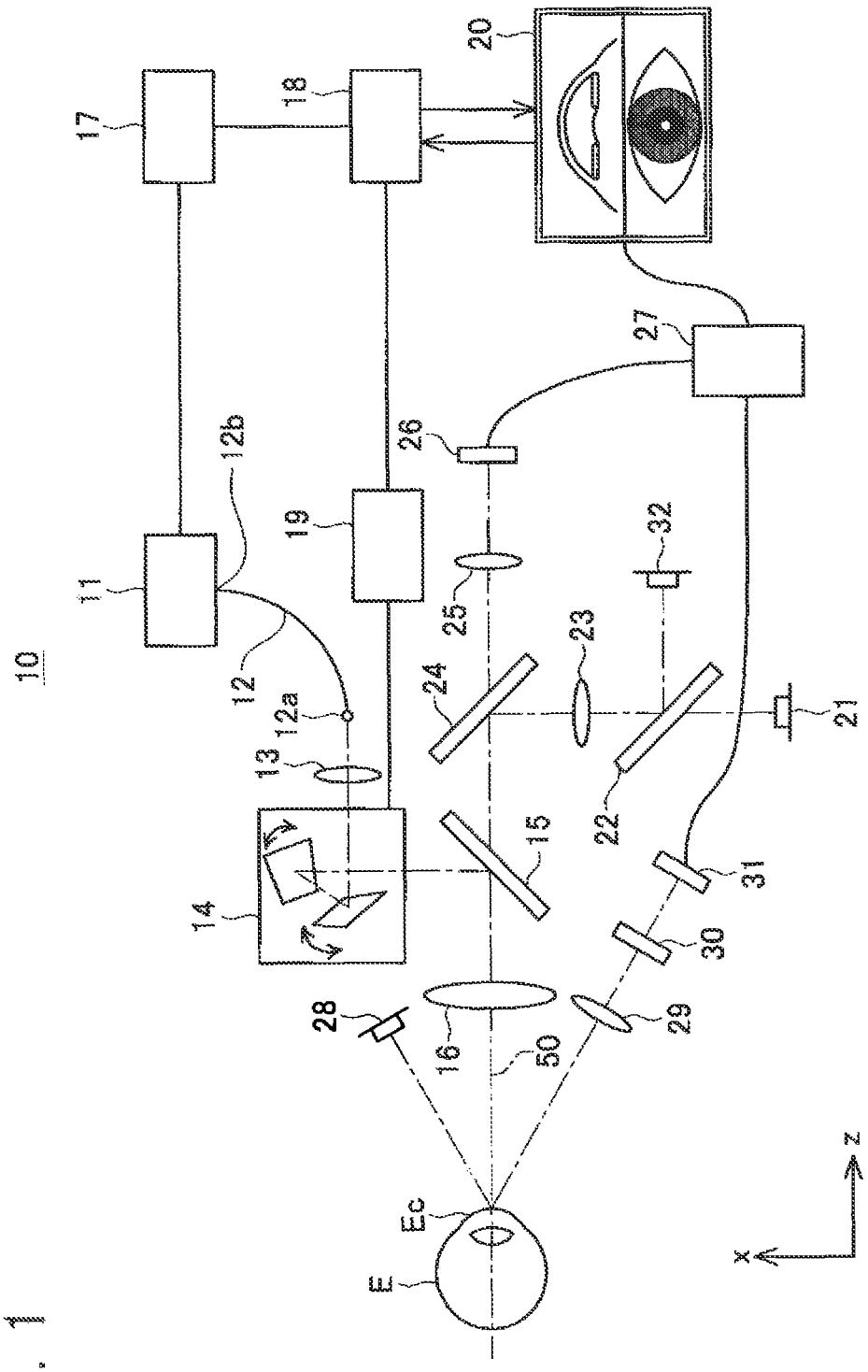
FIG. 1 is a schematic configuration diagram of an ophthalmologic apparatus according to the present embodiment.

In the ophthalmologic apparatus disclosed in the present description, when the eye has been determined to be in the examinable state, the controller may examine the eye with the optical measurement system and imaging device. With such a configuration, since the examination is performed when the eye has been determined to be in the examinable state, failed examination is prevented form being performed.

The ophthalmologic apparatus disclosed in the present description may further include a warning unit that warns an operator that the eye is not in the examinable state. Where such a configuration is used, when the controller determines that the eye is not in the examinable state, the controller may warn the operator that the eye is not in the examinable state by the warning unit. With such a configuration, the operator's attention can be attracted to the fact that the eye is not in the examinable state.

The ophthalmologic apparatus disclosed in the present description may further include a corneal top detecting unit that detects a position of a corneal top of the eye. When such a configuration is used, the drive unit may position the optical measurement system such that the position of the corneal top detected by the cortical top detecting unit is positioned at a reference position preset in the two-dimensional cross sectional image obtained by the imaging unit, and the controller may determine whether the eye is in the examinable state or not based on a specific area preset in the two-dimensional cross sectional image, the specific area having a predetermined range in the vertical direction and is a predetermined distance away from the reference position in the vertical direction. With such a configuration, adequate determination can be made because the area used for determining whether the eye is in the examinable state is cut out from the acquired two-dimensional cross-sectional image with reference to the position of the corneal top of the eye.

For example, the ophthalmologic apparatus disclosed in the present description may be configured to perform at least a keratoscopy that measures the corneal shape of the eye, and a gonioscopy that measures the angle shape of the eye. The controller may be configured such that when the keratoscopy is performed, the controller determines whether the eye is in the examinable state or not based on a first specific area of the two-dimensional cross sectional image, the first specific area having a first range in the vertical direction and is a first distance away from the reference position in the vertical direction, and when the gonioscopy is performed, the controller determines whether the eye is in the examinable state or not based on a second specific area of the two-dimensional cross sectional image, the second specific area having a second range in the vertical direction and is a second distance away from the reference position in the vertical direction. In this case, the second distance may be longer than the first distance. In the keratoscopy, the specific area of the two-dimensional cross sectional image should be narrower and at a shorter distance from the corneal top than in the gonioscopy. Meanwhile, in the gonioscopy, the specific area of the two-dimensional cross sectional image should be wider and at a longer distance from the corneal top than in the keratoscopy. Therefore, by making the second distance longer than the first distance, it is possible to determine adequately whether the eye is in the examinable state according to the examination contents.

In another aspect of the present teachings, an ophthalmologic apparatus disclosed in the present description includes: an optical measurement system that radiates measurement light to an eye to be examined, a drive unit that moves the optical measurement system relative to the eye, an imaging unit that takes a cross sectional image of the eye by using reflected light of the measurement light from the eye, and a controller that controls the drive unit and the imaging unit.

(1) When the drive unit positions the optical measurement system relative to the eye, the controller obtains a two-dimensional cross sectional image by the imaging unit, one axis of the two-dimensional cross sectional image extending in a vertical direction of the eye, and another axis of the two-dimensional cross sectional image extending in a depth direction of the eye, and (2) when the two-dimensional cross sectional image shows that the eye is not in an examinable state, the controller warns an operator that the eye is not in the examinable state. With such an ophthalmologic apparatus, whether the eye is in the examinable state can be also determined even when the eye is dry, opaque, or of an irregular shape, and the controller can warn the operator that the eye is not in the examinable state.

For example, an optical interferometer in which the reflected light of the radiated measurement light from the eye and the reference light are combined and one-dimensional cross sectional information in the depth direction of the eye is acquired from the interfering light thus obtained may be used as the imaging device used in the ophthalmologic apparatuses disclosed in the present description. In such a case, the two-dimensional cross sectional image of the eye can be acquired by scanning the measurement light in a predetermined direction of the eye with the optical measurement system and, at the same time, acquiring the one-dimensional cross sectional information with the optical interferometer. Alternatively, an imaging device may be used that takes a projection cross section of the slit light radiated to the eye. In this case, the eye is irradiated with the slit light by the optical measurement system. The imaging device can be an imaging element that has an optical axis inclined relative to the optical axis of the slit light radiated to the eye and takes the projection cross section obtained with the slit light.

(Embodiment) As shown in FIG. 1, an ophthalmologic apparatus 10 of the present embodiment examines a corneal shape and angle shape of an eye E to be examined. The ophthalmologic apparatus 10 is provided with an optical interferometer 11, an optical measurement system (12, 13, 14, 15, 16) for radiating the measurement light from the optical interferometer 11 to the eye E, an optical xy direction position detecting system (15, 16, 21, 22, 23, 24, 25, 26) for detecting the position of the optical measurement system in xy directions relative to the eye E, an optical z direction position detecting system (28, 29, 30, 31) for detecting the position of the optical measurement system in a z direction relative to the eye E, an optical anterior eye part imaging system (15, 16, 24, 25, 26, 28) that takes the anterior eye part of the eye E, and an optical fixation lamp system (15, 16, 22, 23, 24, 32) for fixing the eye E. The x direction is the transverse direction of the eye E (i.e., direction connecting the left and right eyes (shown in FIG. 1)). The y direction is the vertical direction of the eye E (i.e., up-down direction (direction perpendicular to the paper sheet in FIG. 1)). The z direction is the direction along which the optical measurement system comes closer to or gets farther from the eye E (shown in FIG. 1).

A well-known optical interferometer can be used as the optical interferometer 11. For example, the optical interferometer 11 can be constituted by a light source, a beam splitter, a reference mirror, and a photo detector. In this case, the light from the light source is divided in two by the beam splitter, one beam (that is, the measurement light) is radiated via the optical measurement system to the eye E, and the other beam (that is, the reference light) is radiated to the reflective mirror. The photo detector detects interfering light between the reflected light reflected from the eye E (i.e., reflected light of the radiated measurement light) and the reflected light reflected from the reflective mirror. The output from the photo detector is inputted to a below-described controller 40. The optical interferometer 11 may be of a time domain system or a Fourier domain system.

The optical measurement system has a function of radiating measurement light outgoing from the optical interferometer 11 to the eye E and guiding the reflected light from the eye E to the optical interferometer 11. The optical measurement system is provided with an optical fiber 12, a collimator lens 13, a galvano scanner 14, a hot mirror 15, and an objective lens 16. The optical fiber 12 is connected to one end 12b of the optical interferometer 11. The measurement light outgoing from the optical interferometer 11 is guided from the one end 12b of the optical fiber 12 to the other end 12a and emitted from the other end 12a of the optical fiber 12. The measurement light outgoing from the other end 12a of the optical fiber 12 is radiated to the eye E via the collimator lens 13, galvano scanner 14, hot mirror 15, and objective lens 16. The reflected light of the radiated measurement light from the eye E is guided to the other end 12a of the optical fiber 12 via the objective lens 16, hot mirror 15, galvano scanner 14, and collimator lens 13. The reflected light guided to the other end 12a of the optical fiber 12 is guided by the optical fiber 12 to the optical interferometer 11.

The galvano scanner 14 disposed in the optical measurement system is constituted by a pair of galvano mirrors. Each galvano mirror is driven by the controller 40 (shown in FIG. 2), and the inclination angle thereof relative to the optical axis is changed. Where the galvano mirrors are driven, the measurement light radiated to the eye E is scanned in the x direction and y direction.

An xy direction position optic detection system is constituted by the hot mirror 15, the objective lens 16, a light source 21, a cold mirror 22, a relay lens 23, a half mirror 24, an image forming lens 25, and a CCD camera 26. For example, a LED light source with a center wavelength of 800 nm is used as the light source 21. The light emitted from the light source 21 is radiated to the eye E via the cold mirror 22, relay lens 23, half mirror 24, hot mirror 15, and objective lens 16. The reflected light from the eye E is detected by the CCD camera 26 via the objective lens 16, hot mirror 15, half mirror 24, and image forming lens 25. The output from the CCD camera 26 is inputted to the controller 40. As follows from above, the hot mirror 15 reflects the light outgoing from the optical interferometer 11 and transmits the light from the light source 21. Further, the hot mirror 15 also transmits the light from the below-described light sources 28, 32. Therefore, the reflected light of the light from the light sources 21, 28, 32 (i.e., reflected light from the eye E) is guided to the optical interferometer 11.

The z direction position optic detection system is constituted by a light source 28, an image forming lens 29, an infrared radiation transmitting filter 30, and a line sensor 31. For example, a LED light source with a center wavelength of 940 nm, which emits infrared light, can be used as the light source 28. The light source 28 is disposed so as to radiate light obliquely to the eye E. Part of the light radiated from the light source 28 to the eye E is mirror reflected at the surface of a cornea Ec of the eye E, and the mirror-reflected light is detected by the line sensor 31 via the image forming lens 29 and infrared radiation transmitting filter 30. The output from the line sensor 31 is inputted to the controller 40. In this case, the infrared radiation transmitting filter 30 transmits the light from the light source 28, but blocks the light from the light source 21. Therefore, the light from the light source 21 for detecting the xy direction position is not detected by the line sensor 31.

The optical anterior part imaging system is constituted by the hot mirror 15, objective lens 16, half mirror 24, image converging lens 25, CCD camera 26, and light source 28. The anterior part image of the eye E that is obtained with the light emitted from the light source 28 is detected by the CCD camera 26 via the objective lens 16, hot mirror 15, half mirror 24, and image converging lens 25. The anterior part image of the eye E that is detected by the CCD camera 26 is inputted to the device 40. As follows from the above, the CCD camera 26 can detect simultaneously the reflected image from the eye E that is created by the light from the light source 21 (i.e., light source for xy direction position detection) and the reflected image (i.e., anterior part image) from the eye E that is created by the light from the light source 28 (i.e., light source for anterior part imaging).

The optical fixation lamp system is constituted by the hot mirror 15, objective lens 16, cold mirror 22, relay lens 23, half mirror 24, and a fixation lamp 32. For example, a LED light source with a center wavelength of 520 nm, which emits visible light, can be used as the fixation lamp 32. The light emitted from the fixation lamp 32 is radiated to the eye E via the cold mirror 22, relay lens 23, half minor 24, hot mirror 15, and objective lens 16. Where the patient views the light from the fixation lamp 32, the eye E is fixed. The half mirror 24 transmits part of the light from the light source 21, 28, reflects the remaining light from these sources, and completely reflects the light of the fixation lamp 32. Therefore, the reflected light of the light emitted from the fixation lamp 32 that has been reflected from the eye E is not detected by the CCD camera 26.

The ophthalmologic apparatus 10 is provided with a position adjustment mechanism 35 (shown in FIG. 2) for adjusting the positions of the optical systems (more specifically, the optical measurement system, xy direction position optic detection system, z direction position optic detection system, optical anterior part imaging system, and optical fixation lamp system) relative to the eye E and a drive mechanism 34 (shown in FIG. 2) that drives the position adjustment mechanism 35. By driving the position adjustment mechanism 35 with the driver 34, it is possible to arrange the optical systems at predetermined scanning positions relative to the eye E. In a state in which the optical systems of the ophthalmologic apparatus 10 are disposed at the scanning positions, the light from the light sources 21, 32 is radiated into the eye E from the front surface thereof, and the light of the light source 28 is radiated at a predetermined angle to the eye E. Further, the measurement light emitted from the optical interferometer 11 to the eye E is scanned by the galvano scanner 14 in the x direction and y direction about the corneal top of the eye E.

Figure 2:
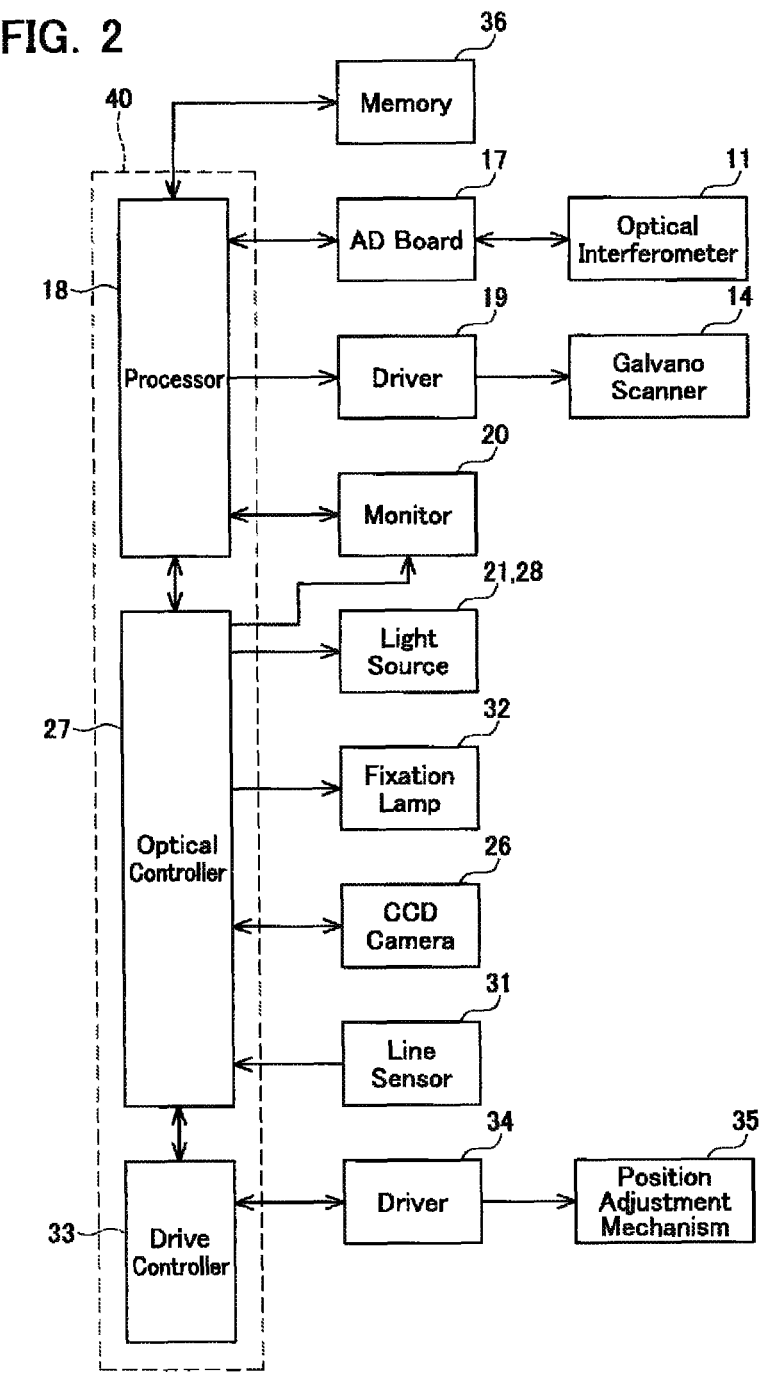
FIG. 2 is a block-diagram of the control system of the ophthalmologic apparatus according to the present embodiment.

The configuration of the control system of the ophthalmologic apparatus 10 will be explained below. As shown in FIG. 2, the ophthalmologic apparatus 10 is provided with the controller 40 that controls various units of the ophthalmologic apparatus 10. The controller 40 is provided with a calculation unit 18 that acquires the cross sectional image of the eye E, an optical controller 27 that controls optical systems, and a drive controller 33 (shown only in FIG. 2) that controls the driver 34. Further, the controller 40 may comprise a processor and a memory that stores a program. When the processor executes the program stored in the memory, the processor can function as the calculation unit 18, the optical controller 27, and the drive controller 33.

The calculation unit 18 is connected to the optical interferometer 11 by an AD board 17. The calculation unit 18 performs ON/OFF control of the optical interferometer 11 via the AD hoard 17. Information relating to the interfering light acquired by the optical interferometer 11 (i.e., one-dimensional cross sectional information in the z direction (i.e., depth direction of the eye E)) is inputted via the AD board 17 to the calculation unit 18. Thus, the interfering light detected by the optical interferometer 11 is inputted as an electric signal (analog signal) to the AD board 17. The electric signal (analog signal) inputted to the AD board 17 is converted into a digital signal and the converted digital signal is inputted to the calculation unit 18.

The galvano scanner 14 is connected by the drive circuit 19 to the calculation unit 18. Since the calculation unit 18 drives the galvano scanner 14 via the drive circuit 19, the measurement light radiated from the optical interferometer 11 to the eye E is scanned in the x direction (i.e., transverse direction of the eye E) and y direction (i.e., vertical direction of the eye E). By acquiring the one-dimensional cross sectional information outputted from the optical interferometer 11, while scanning the measurement light radiated to the eye E in the x direction, it is possible to acquire the two-dimensional cross sectional image in the x direction (i.e., transverse direction) and z direction (i.e., depth direction) of the eye E. Further, by acquiring the one-dimensional cross sectional information outputted from the optical interferometer 11, while scanning the measurement light radiated to the eye E in the y direction, it is possible to acquire the two-dimensional cross sectional image in the y direction (i.e., vertical direction) and z direction (i.e., depth direction) of the eye E. The calculation unit 18 determines whether the eye E is in the examinable state or not on the basis of the two-dimensional cross sectional image in the y direction and z direction of the eye E that has been acquired when positioning the optical systems. The procedure of determining whether the eye E is in the examinable state or not will be described below. A well-known method can be used for acquiring the two-dimensional cross sectional image from the one-dimensional cross sectional image outputted from the optical interferometer 11.

A monitor 20 and a memory 36 are also connected to the calculation unit 18. The calculation unit 18 can display the two-dimensional cross sectional image acquired on the basis of detection results of the optical interferometer 11 on the monitor 20 or can store the two-dimensional cross sectional image in the memory 36.

The light sources 21, 28, fixation lamp 32, CCD camera 26, line sensor 31, and monitor 20 are connected to the optical controller 27. The optical controller 27 performs ON/OFF control of the light sources 21, 28 and also performs ON/OFF control of the fixation lamp 32. Further, signals from the CCD camera 26 and signals from the line sensor 31 are inputted to the optical controller 27. The optical controller 27 detects the positions of the optical systems in the xy directions relative to the eye E on the basis of the signals from the CCD camera 26, acquires the image of the anterior part of the eye E, and outputs the acquired image to the monitor 20. Further, the optical controller 27 detects the position of the optical systems in the z direction relative to the eye E on the basis of the signal from the line sensor 31. A configuration for detecting the positions of the optical systems in the xy directions and z direction relative to the eye E is not limited to the abovementioned configuration using the CCD camera 26 and line sensor 31, and such detection can be performed with other well-known conventional configurations.

The drive controller 33 drives the position adjustment mechanism 35 with the driver 34 on the basis of the positions of the optical systems detected by the optical controller 27 (that is, positions in the xyz directions relative to the eye E). As a result, the optical systems are positioned at the predetermined examination positions relative to the eye E.

Figure 3:
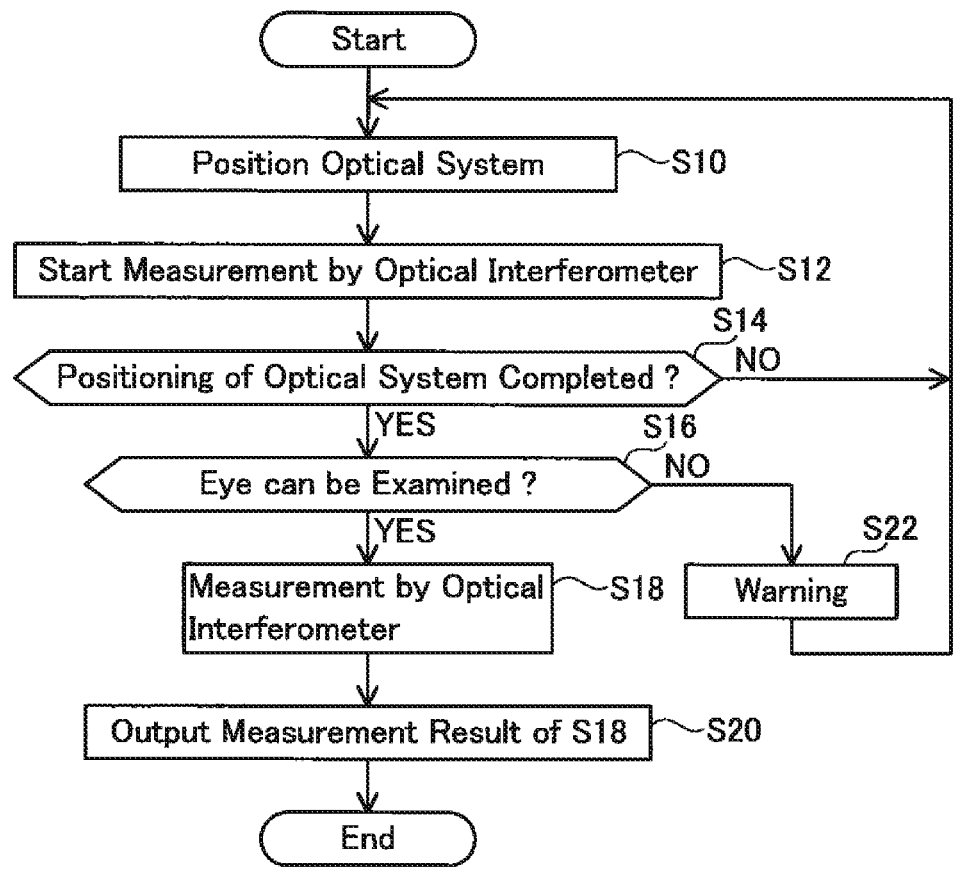
FIG. 3 is a flowchart illustrating an example of processing procedure in the ophthalmologic apparatus according to the present embodiment.

The procedure of examining (measuring) the conical shape and angle shape by using the ophthalmologic apparatus 10 will be explained below with reference to FIG. 3. First, the operator operates an input device such as a switch (not shown in the figure) and instructs the controller 40 do perform the examination of corneal shape or angle shape. As a result, the controller 40 drives the position adjustment mechanism 35 with the driver 34 and starts positioning the optical systems (that is, the optical measurement system, xy direction position optic detection system, z direction position optic detection system, optical anterior part imaging system, and optical fixation lamp system) relative to the eye E (S10). Thus, the controller 40 detects the position of the optical systems in the xy direction relative to the eye E with the xy direction position optic detection system and detects the position of the optical systems in the z direction relative to the eye E with the z direction position optic detection system and drives the position adjustment mechanism 35 with the driver 34 on the basis of the detected positions of the optical systems in the xyz direction so that the positions of the optical systems relative to the eye E become the predetermined examination positions.

Where the positioning of the optical systems relative to the eye E is started, the controller 40 starts measurements with the optical interferometer 11 (S12). Thus, the controller 40 scans the measurement light in the vertical direction (i.e., y direction) of the eye E by driving the galvano scanner 14 and, at the same time, acquires the one-dimensional cross sectional information with the optical interferometer 11. As a result, the controller 40 acquires the two-dimensional cross sectional image in the yz directions of the eye E.

Then, the controller 40 determines whether the positioning of the optical systems has been complete or not (S14). Where the positioning of the optical systems has been completed (YES in S14), the processing advances to step S16. Where the positioning of the optical systems has not been complete (NO in S14), the processing returns to step S10 and the processing is repeated starting from step S10. The driver 34 thus drives the position adjustment mechanism 35 till the position of the optical system relative to the eye E comes to be at the predetermined examination positions. Further, the optical interferometer 11 acquires the two-dimensional cross sectional image in the yz directions as long as the positioning of the optician systems relative to the eye E is performed.

Figure 4A:
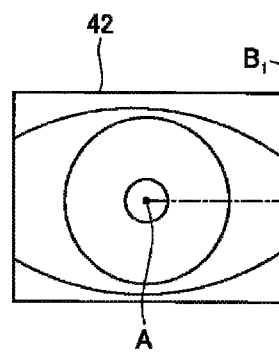
FIG. 4(a) shows an anterior eye part image and FIG. 4(b) shows a a two-dimensional cross sectional image in the case where the eye is in the examinable state.
Figure 4B:
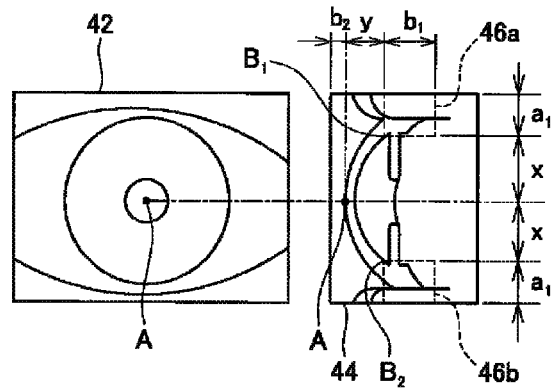
Figure 5A:
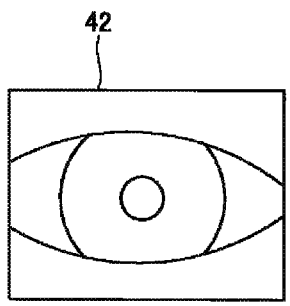
FIG. 5(a) shows the anterior eye part image and FIG. 5(b) shows the two-dimensional cross sectional image in the case where the eye is not in the examinable state.
Figure 5B:
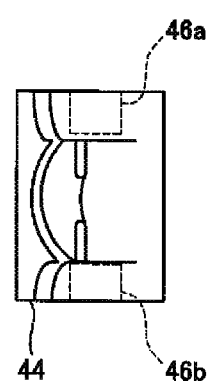

In the present embodiment, in a state in which the optical systems have been positioned relative to the eye E, the top of the cornea Ec of the eye E is adjusted so as to be positioned in the center of the anterior eye part image 42 (shown in FIGS. 4A and 5A) taken by the CCD camera 26 and so as to be positioned at the predetermined reference position within the two-dimensional cross sectional image 44 (shown in FIGS. 4B and 5B) obtained by the optical interferometer 11. More specifically, as shown in FIG. 4B, the top A of the cornea Ec of the eye E assumes a center position in the y direction (i.e., vertical direction) in the two-dimensional cross sectional image 44 obtained by the optical interferometer 11 and a position at a distance of b2 from the left end of the image in the z direction (i.e., depth direction).

Where the positioning of the optical systems relative to the eye E is completed, the controller 40 determines whether the eye F is in the examinable state or not (S16). More specifically, this determination is made on the basis of whether or not a structural body (for example, iris and conjunctiva) constituting the eye E is present in the preset determination areas 46a, 46b in the two-dimensional cross sectional image 44 in the yz directions acquired in step S12 in the period in which the positioning has ended (see FIGS. 4 and 5).

Thus, in the present embodiment, in a state in which the optical systems are positioned relative to the eye E, the top A of the cornea Ec of the eye E is at a predetermined reference position within the two-dimensional cross sectional image 44. Therefore, where the determination areas 46a, 46b are set with reference to the top A of the cornea Ec of the eye E within the two-dimensional cross sectional image 44, it can be configured such that, when the eye E is in the examinable state, the structural body appears in the determination areas 46a, 46b, and when the eye E is not in the examinable state, the structural body does not, appear in the determination areas 46a, 46b. By determining whether or not the structural body appears in the determination areas 46a, 46b that have thus been set, it is possible to determine whether the eye E is in the examinable state or not.

For example, as shown in FIGS. 4A, 4B, 5A and 5B, the areas with a width $a_1$ from points $B_1$, $B_2$ in the vertical direction and a width $b_1$ in the depth direction are set as the determination areas 46a, 46b, where the points $B_1$, $B_2$ are at a distance x in the vertical direction and at a distance y in the depth direction from the top A of the cornea Ec in the two-dimensional cross sectional image 44. Where the determination areas 46a, 46b are thus set, when a structural body appears in the determination areas 46a, 46b (e.g., the case shown in FIGS. 4A and 4B), it is possible to determine that the eyelid of the eye E is sufficiently open and the eye F is in the examinable state. By contrast, where the structural body does not appear in the determination areas 46a, 46b (e.g., the case shown in FIGS. 5A and 5B), it is possible to determine that the eyelid of the eye E is not sufficiently open and the eye E is not in the examinable state. Therefore, by determining whether or not the structural body has appeared in the determination areas 46, 46*b* that have been set with the top A of the cornea Ec as reference, it is possible to determine whether the eye E is in the examinable state or not.

Various methods can be used to determine whether the structural body has appeared in the determination areas 46*a*, 46*b*. For example, when the structural body has appeared in the determination areas 46*a*, 46*b* (e.g., the case shown in FIGS. 4A and 4B), a group of pixels with a high brightness is present in the determination areas 46*a*, 46*b*. By contrast, where the structural body has not appeared in the determination areas 46*a*, 46*b* (e.g., the case shown in FIGS. 5A and 5B), no group of pixels with a high brightness is present in the determination areas 46*a*, 46*h*. Accordingly, when the sum total of brightness values of pixels within the determination areas 46*a*, 46*b* is calculated and the value obtained is equal to or higher than a predetermined threshold, it can be determined that the structural body has appeared in the determination areas 46*a*, 46*b*, and when the aforementioned value is less than the predetermined threshold, it can be determined that the structural body has not appeared in the determination areas 46*a*, 46*b*.

When the eye E has been determined to be in the examinable state (YES in S16), the controller 40 drives the galvano scanner 14 with the drive circuit 19, thereby scanning the measurement light within the desirable range (x direction and/or y direction) of the eye and at the same time acquires one-dimensional cross sectional information with the optical interferometer 11 (S18). As a result, the cross-sectional image necessary for performing the diagnostic of the eye E is acquired by the optical interferometer 11, and the acquired cross sectional image is stored in the memory 36 and displayed on the monitor 20 (S20). As a result, the cross sectional image of the desired position is displayed on the monitor 20 and the diagnostic of eye E to be examined can be performed by the ophthalmologist or the like. Meanwhile, when the eye E has been determined not to be in the examinable state (NO in S16), the controller 40 displays on the monitor 20 that the eye is not in the examinable state (S22), returns to step S10, and implements the processing from step S10. Since it is displayed on the monitor 20 in step S22 that the eye is not in the examinable state, the operator can ask the patient to open the eye, and the desired image can be easily obtained by processing from the next step S10.

As described hereinabove, in the ophthalmological apparatus 10 of the present embodiment, whether the eye E is in the examinable state or not is determined by using the two-dimensional cross sectional image in the yz directions obtained by the optical interferometer 11. Therefore, even when the eye E is dry; opaque, or of an irregular shape, a two-dimensional cross sectional image necessary for determining the state of the eye E can be obtained. As a result, whether the eye E is in the examinable state or not can be accurately determined.

Specific embodiment of the present teachings is described above, but this merely illustrates some representative possibilities for utilizing the invention and does not restrict the claims thereof. The subject matter set forth in the claims includes variations and modifications of the specific examples set forth above.

For example, in the aforementioned embodiment; the determination areas 46*a*, 46*b* are set at both sides in the vertical direction of the corneal top A of the eye E, but the determination area may be set only above the corneal top. By setting the determination area only above the corneal top, it is possible to simplify the determination processing by comparison with that in the case where the determination areas are set both above and below the corneal top. Further, where the determination area is provided above the corneal top of the eye, the state of upper eyelid that greatly effects the examination can be determined. Therefore, although the processing is simple, the state of the eye can be adequately evaluated.

Further, in the above-described embodiment, the determination areas 46*a*, 46*b* that are used during examination of the cornea shape are same as the determination areas 46*a*, 46*b* used when examining the angle shape, but the determination areas 46; 46*b* can be set as appropriate according to the type of examination. For example, when the cornea shape is examined, the opening of eyelid may be less than that when the angle shape is examined. Therefore, the "distance x1 in the vertical direction from the corneal top A to the points $B_1$, $B_2$ of the determination areas 46*a*, 46*b*" that is used when the cornea shape is measured can be set to be less than the "distance x2 in the vertical direction from the corneal top A to the points $B_1$, $B_2$ of the determination areas 46*a*, 46*b*" that is used when the angle shape is measured. By thus setting the determination areas 46*a*, 46*b* according to the type of the examination, it is possible to determine adequately whether the eye is examinable or not.

Further, in the above-described embodiment, the two-dimensional cross sectional image of the eye E is continuously acquired by the optical interferometer 11, while the optical system is positioned relative to the eye E, but the two-dimensional cross sectional image of the eye E may be also acquired by the optical interferometer 11 after the optical system has been positioned relative to the eye E. With such a configuration, whether the eye E is in the examinable state or not can still be adequately determined.

Further, in the above-described embodiment, when the eye is not in the examinable state, such is displayed on the monitor 20, but the operator can be also notified of it by sound.

Further, in the above-described embodiment, the optical interferometer is used to obtain a two-dimensional cross sectional image of the eye, but the two-dimensional cross sectional image of the eye may be also obtained by other configurations. For example, the two-dimensional cross sectional image of the eye may be acquired by taking a projection cross sectional image obtained with the slit light radiated to the eye. For example, the optical measurement system can be configured to radiate slit light to the eye. An imaging element has an optical axis inclined relative to the optical axis of the slit light radiated to the eye and takes the projection cross section obtained with the slit light.

What is claimed is:

1. An ophthalmologic apparatus comprising:
   an optical measurement system that radiates measurement light to an eye to be examined,
   a drive unit that moves the optical measurement system relative to the eye,
   an imaging unit that takes a cross sectional image of the eye by using reflected light of the measurement light from the eye,
   a detecting unit that detects a position of a corneal top of the eye, and
   a controller that controls the drive unit and the imaging unit, wherein
   when the drive unit positions the optical measurement system relative to the eye, the controller obtains a two-dimensional cross sectional image by the imaging device, one axis of the two-dimensional cross sectional image extending in a vertical direction of the eye, and
   wherein the drive unit positions the optical measurement system such that the position of the corneal top detected by the detecting unit is positioned at a reference position preset in the two-dimensional cross sectional image obtained by the imaging unit, and the controller determines whether the eye is in an examinable state or not based on a specific area preset in the two-dimensional cross sectional image, the specific area having a predetermined range in the vertical direction and is a predetermined distance away from the reference position in the vertical direction.

2. The ophthalmologic apparatus as in claim 1, further comprising a warning unit that warns an operator that the eye is not in the examinable state, wherein when the controller determines that the eye is not in the examinable state, the controller warns the operator by the warning unit.

3. The ophthalmologic apparatus as in claim 1, wherein the ophthalmologic apparatus performs a keratoscopy that measures the corneal shape of the eye, and a gonioscopy that measures the angle shape of the eye, wherein when the keratoscopy is performed, the controller determines whether the eye is in the examinable state or not based on a first specific area of the two-dimensional cross sectional image, the first specific area having a first range in the vertical direction and is a first distance away from the reference position in the vertical direction, when the gonioscopy is performed, the controller determines whether the eye is in the examinable state or not based on a second specific area of the two-dimensional cross sectional image, the second specific area having a second range in the vertical direction and is a second distance away from the reference position in the vertical direction, and the second distance is longer than the first distance.

4. An ophthalmologic apparatus comprising:

an optical measurement system that radiates measurement light to an eye to be examined, a drive unit that moves the optical measurement system relative to the eye, an imaging unit that takes a cross sectional image of the eye by using reflected light of the measurement light from the eye, a detecting unit that detects a position of a corneal top of the eye, and a controller that controls the drive unit and the imaging unit, wherein when the drive unit positions the optical measurement system relative to the eye, the controller obtains a two-dimensional cross sectional image by the imaging device, one axis of the two-dimensional cross sectional image extending in a vertical direction of the eye, and another axis of the two-dimensional cross sectional image extending in a depth direction of the eye, wherein the drive unit positions the optical measurement system such that the position of the corneal top detected by the detecting unit is positioned at a reference position preset in the two-dimensional cross sectional image obtained by the imaging unit, the controller determines whether the eye is in an examinable state or not based on a specific area preset in the two-dimensional cross sectional image, the specific area having a predetermined range in the vertical direction and is a predetermined distance away from the reference position in the vertical direction, and when the two-dimensional cross sectional image shows that the eye is not in an examinable state, the controller warns an operator that the eye is not in the examinable state.

\* \* \* \* \*